(12) United States Patent
Venkateshwaran et al.

(10) Patent No.: US 6,727,401 B1
(45) Date of Patent: Apr. 27, 2004

(54) PRESSURE SENSITIVE ADHESIVE MATRIX PATCH FOR THE TREATMENT OF ONYCHOMYCOSIS

(75) Inventors: Srinivasan Venkateshwaran, Salt Lake City, UT (US); Danyi Quan, Salt Lake City, UT (US)

(73) Assignee: Watson Pharmaceuticals, Inc., Corona, CA (US)

( * ) Notice: Subject to any disclaimer, the term of this patent is extended or adjusted under 35 U.S.C. 154(b) by 0 days.

(21) Appl. No.: 09/022,504

(22) Filed: Feb. 12, 1998

(51) Int. Cl.[7] ................................................. A61F 13/00
(52) U.S. Cl. ......................... 602/41; 424/448; 424/449
(58) Field of Search ............................. 602/41, 22, 30, 602/31; 424/404, 443, 445–449

(56) References Cited

U.S. PATENT DOCUMENTS

| | | | |
|---|---|---|---|
| 3,731,683 A | | 5/1973 | Zaffaroni |
| 5,162,037 A | | 11/1992 | Whitson-Fischman |
| 5,181,914 A | | 1/1993 | Zook |
| 5,330,452 A | | 7/1994 | Zook |
| 5,415,866 A | | 5/1995 | Zook |
| 5,415,903 A | | 5/1995 | Hoffman et al. |
| 5,464,610 A | * | 11/1995 | Hayes, Jr. et al. ............. 424/61 |
| 5,497,789 A | | 3/1996 | Zook |
| 5,652,256 A | | 7/1997 | Knowles |
| 5,696,164 A | * | 12/1997 | Sun et al. .................... 514/562 |
| 5,753,256 A | | 5/1998 | Cordes et al. |
| 5,773,028 A | * | 6/1998 | Inagi et al. |

FOREIGN PATENT DOCUMENTS

| | | |
|---|---|---|
| EP | 0 515 312 A2 | 5/1992 |
| WO | WO 87/02580 | 5/1987 |
| WO | WO 95/23597 | 9/1995 |

OTHER PUBLICATIONS

J Faergemann, H Zehender, and L Millerioux, Levels of terbinafine in plasma, stratum corneum, dermis–epidermis (without stratum corneum), sebum, hair and nails during and after 250 mg terbinafine orally once daily for 7 and 14 days. *Clinical and Experimental Dermatology*, 19:121–126, 1994.
H P Baden, The Physical Properties of Nail. *The Journal of Investigative Dermatology*, 55(2): 115–122.
M Johnson, J S Comaish, and S Shuster, Nail is Produced by the Normal Nail Bed: A Controversy Resolved. *British Journal of Dermatology*, 125: 27–29, 1991.
D S Walters, and R K Scher, Nail Terminology. *International Journal of Dermatology*, 34(9): 607–610, 1995.

* cited by examiner

Primary Examiner—Weilun Lo
Assistant Examiner—Michele Kidwell
(74) Attorney, Agent, or Firm—Thorpe, North & Western, LLP

(57) ABSTRACT

A device for treating antifungal infections of toenails and fingernails is made up of an occlusive backing layer and a pressure sensitive adhesive matrix layer in which is uniformly dispersed an effective amount of an antifungal agent and, optionally, a chemical enhancer. The matrix layer has a first surface adhering to the backing layer and a second surface adapted to be in diffusional contact with the infected nail and surrounding skin area. The device is configured, when applied, to cover and adhere to the nail and surrounding skin areas for an extended period of time without causing irritation to the skin or inhibiting normal physical activity while providing a continuous delivery of antifungal agent to the infected area.

10 Claims, 2 Drawing Sheets

PRESSURE SENSITIVE ADHESIVE MATRIX PATCH FOR THE TREATMENT OF ONYCHOMYCOSIS

FIELD OF THE INVENTION

This invention relates to a device for the administration of a pharmaceutical composition for treating fungal nail infections. Particularly, the device has an occlusive backing which facilitates the composition's migration into finger nails, toe nails and the epidermis around the nails.

BACKGROUND OF THE INVENTION

Conditions such as onychomycosis pose serious problems in dermatology. Onychomycosis is a condition recognized by discoloration beneath toe nails and finger nails along with pain when pressure is placed near or at the site of discoloration. The condition usually affects more than one nail. Various fungi, classified as white superficial fungi, cause the condition. The prevalence of onychomycosis in the general population is in the range of 2–13% and increases to about 15–20% in the 40–60 year old age group.

The current treatment of onychomycosis generally falls into three categories: systemic administration of antifungals; surgical removal of all or part of the nail followed by topical treatment of the exposed tissue; or topical application of conventional creams, lotions, gels or solutions on the infected nail, frequently including the use of bandages to keep these dosage forms in place on the nails. All of these approaches have major drawbacks.

Long term systemic (oral) administration of an antifungal agent for the treatment of onychomycosis has been required to produce a therapeutic effect. For example, oral treatment with the antifungal compound ketoconozole typically requires administration of 200 to 400 mg/day for 6 months before any significant therapeutic benefit is realized. Such long term, high dose systemic therapy can have significant adverse effects. For example, ketoconozole has been reported to have liver toxicity effects and reduces testosterone levels in blood due to adverse effects on the testes. Patient compliance is a problem with such long term therapies especially those which involve serious adverse effects.

Surgical removal of all or part of the nail followed by topical treatment also has severe drawbacks. The pain and discomfort associated with the surgery and the undesirable cosmetic appearance of the nail or nail bed represent significant problems, particularly for female patients or those more sensitive to physical appearance.

Topical therapy has significant problems too. Topical dosage forms such as creams, lotions, gels etc., do not keep the drug in intimate contact with the nail for prolonged periods of time. Bandages have been used to hold drug reservoirs in place in an attempt to enhance absorption of the pharmaceutical agent. However the bandages are thick, awkward, troublesome and generally lead to poor patient compliance.

Hydrophilic and hydrophobic film forming topical antifungal solutions have also been developed. These dosage forms provide improved contact between the drug and the nail, but the films are not occlusive. Moreover, topical formulations for onychomycosis treatment have exclusively tried to deliver the drug to the target site (an infected nail bed) by diffusion across or through the nail.

Human nail is more like hair than stratum corneum with respect to chemical composition and permeability. Nitrogen is the major component of the nail attesting to the nail's proteinaceous nature. The total lipid content of mature nail is 0.1–1.0%, while the stratum corneum lipid is about 10% w/w. The nail is 100–200 times thicker than the stratum corneum and has a very high affinity and capacity for binding and retaining antifungal drugs. Consequently, little if any drug penetrates through the nail to reach the target site (the nail bed, see FIG. 4, number 16). Because of these reasons, topical therapy for onychomycosis has generally been ineffective.

Onychomycosis is a localized fungal infection of the nail plate and nail bed. The ideal therapy for onychomycosis would maintain very high local tissue concentration of an antifungal agent in the nail and skin, and deliver effective amounts of drug topically to the nail bed, with minimum systemic exposure. Matrix type skin patches are well known in the art, but their advantages for the treatment of onychomycosis have not been recognized. A matrix patch device configured for application over the infected nail and surrounding skin would overcome all the disadvantages of conventional topical therapy for onychomycosis.

It would therefore be desirable to have a matrix patch device which not only enabled the passage of drug compositions into the nail to preclude additional invasive infection but which simultaneously facilitated the transnail and transdermal administration of an antifungal agent to treat the infection directly. The invention herein described accomplishes this and other purposes.

SUMMARY OF THE INVENTION

Accordingly, it is a primary objective of the present invention to provide a method for the transdermal/transnail delivery of sufficient amounts of a suitable drug to an affected nail bed and surrounding tissue.

It is an additional object of the present invention to provide a method whereby an occlusive patch is adhered to the treatment site such that the adhesive layer of the patch is maintained in direct diffusional contact with the digit to be treated and where the adhesive layer is adapted to deliver an antifungal agent to the infected site.

These and other objects may be realized by means of an occlusive device suitable for the transdermal and transnail delivery of antifungal pharmaceutically-active agents which are lipophilic or hydrophilic, including salts. The device comprises an occlusive backing layer and a pressure sensitive matrix layer having a first surface adhering to the backing layer and an opposite second surface adapted to be in diffusional contact with the nail and surrounding skin areas.

Matrix type skin patches are known in the art but none have heretofore been developed and configured for application and adhesion to the nail and surrounding skin areas. It has been discovered that such an antifungal pressure sensitive adhesive matrix patch renders it possible to saturate the nail plate with very high concentration of an antifungal agent compared to systemic dosing (with minimal systemic exposure) while administering the antifungal drug to the nail bed, as the target site, via the nail and skin around the nail at much higher rates than would be possible through the nail alone. The invention provides penetrating transdermal/ transnail compositions based on the use of a pharmaceutically-active agent dissolved in, or admixed with a biocompatible pressure sensitive adhesive. It may also be advantageous and even preferable to also include an effective amount of one or more penetration enhancing agents as will be more specifically identified below.

The drug enhancer combination is contained in an occlusive device for purposes of holding the composition against the skin or nail surface for administration. Such devices are patches configured for adhesion to the nail surface including a portion of the surrounding tissue in matrix form.

A matrix patch is one where in the drug/enhancer is admixed with a pressure sensitive adhesive to form a matrix. Matrix patches are formed by admixing the drug/adhesive and enhancer if present in a fluid or spreadable form. A uniform depth or thickness of admixture is spread or cast on a protective pealable release liner and a film backing is placed on the opposite side of the admixture to form a film sandwich with the drug/adhesive/enhancer in the center. The film sandwich is then die cut into the appropriate size and pouched in a protective pouch until ready for application. For use, the pealable release liner is removed and the drug/adhesive/enhancer matrix is applied directly to the nail and surrounding skin. The drug and enhancer migrate from within the adhesive matrix to the nail and skin surface. The enhancer, as here presented, functions to increase the flux of drug through the skin and increase the penetration of the drug into and through the nail. Importantly, the occlusive backing of the patch holds the drug against the nail and skin to increase the migration of the drug from the matrix patch into the nail and associated skin.

DETAILED DESCRIPTION OF FIGURES

Figure 1:
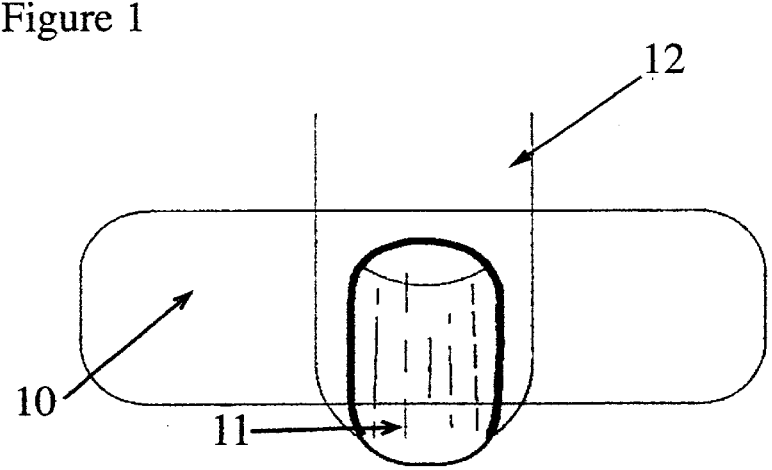
FIG. 1 is a top view of a digit with attached nail and one embodiment of the matrix patch of the present invention.
Figure 2:
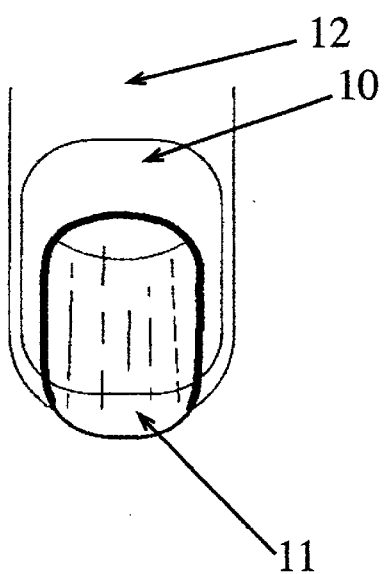
FIG. 2 is a top view similar to FIG. 1 showing a second embodiment of the patch.
Figure 3:
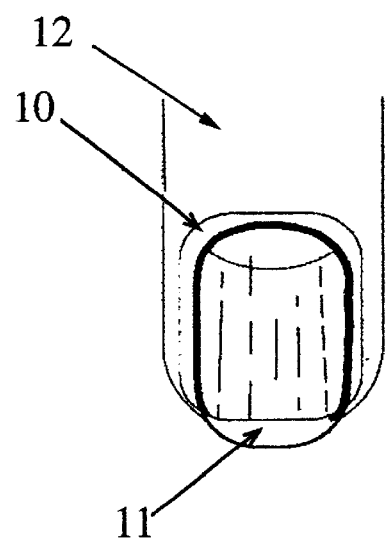
FIG. 3 is a top view similar to FIG. 1 showing a third embodiment of the patch.

FIG. 1 is a top view of a digit 12 with attached nail 11 and one embodiment of the matrix patch, 10 of the present invention. Importantly, it is preferred that the matrix patch cover a portion of the nail, cuticle and epidermis in the nail region. Although the embodiments shown in FIGS. 1, 2 and 3 depict three patch embodiments showing variations as to patch size and geometry, all three illustrate acceptable placement of the drug containing matrix patch. The acceptable placement of the patch is shown to cover a part or all of the infected nail, the cuticle and a portion of the epidermis medial to the nail to be treated. It is important to contact one if not all three of these portions with the drug delivering matrix patch to promote the simultaneous transdermal/transnail delivery of the medication.

Figure 4:
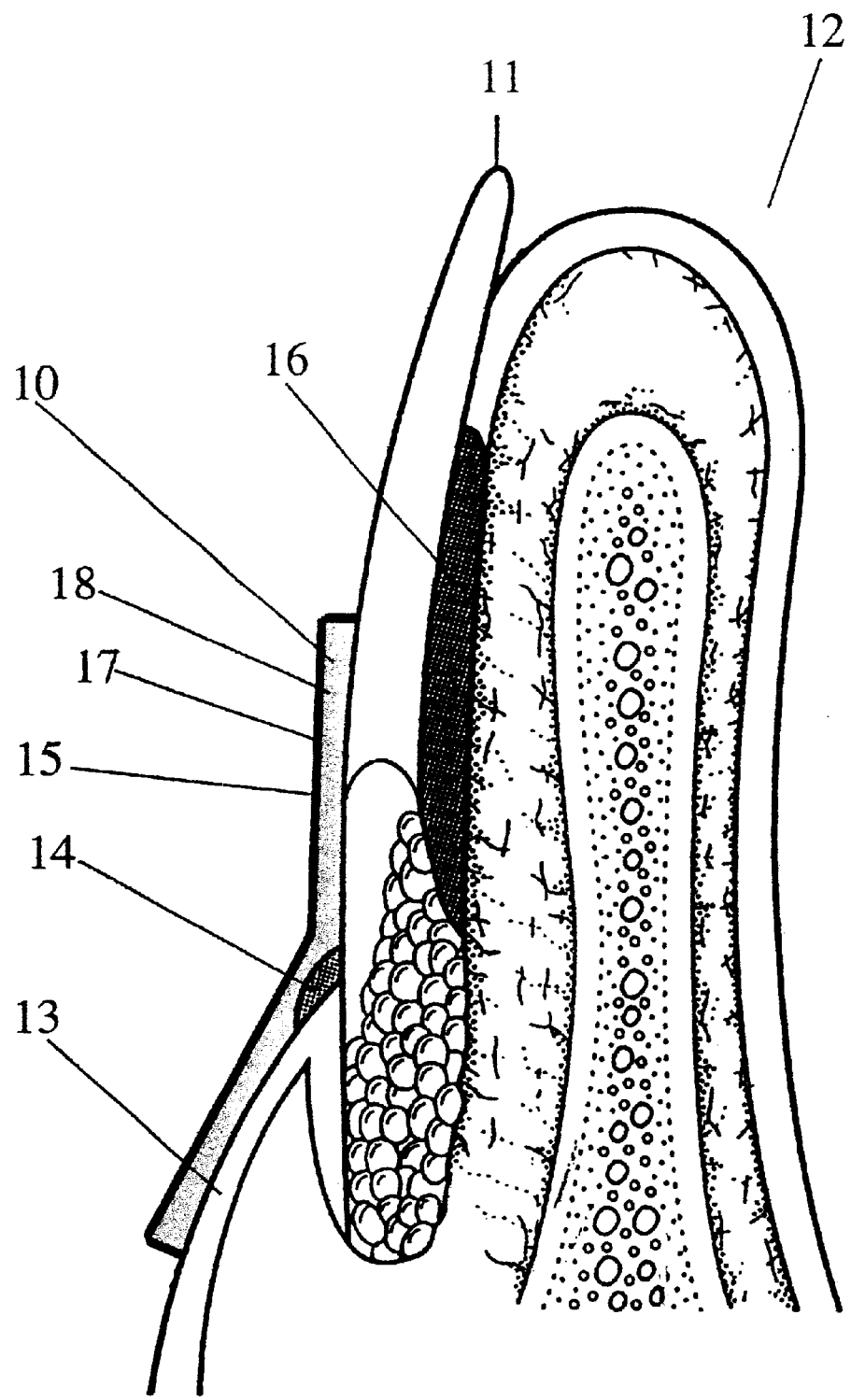
FIG. 4 is a cross sectional view of a digit i.e. a toe, illustrating the nail, nail bed and other anatomical portions of the nail and surrounding skin area for optimal delivery of an antifungal agents; where the matrix patch of the present invention is also shown in cross section with the outer occlusive backing and the matrix portion which contains and delivers the drug to the tissue.

FIG. 4 is a cross sectional view of a digit, 12 with nail 11, epidermis 13, cuticle 14 and nail bed 16. This figure demonstrates the anatomical relationship between the portion of the nail which is typically in need of treatment, the nail bed 16, and the surrounding physical barriers to its direct treatment, the nail 11, epidermis 13 and cuticle 14. These formidable anatomic barriers have, as discussed earlier, prevented meaningful treatment of infections of the nail bed and associated tissues. This figure presents an additional view of a preferred embodiment of the present matrix patch 10 appropriately positioned so as to adherently contact the epidermis 13, cuticle 14, and nail 11. As depicted patch 10 consists of an impermeable backing 17 overlying a matrix layer 18 in which the drug and enhancer, if present, are uniformly distributed. As depicted in one preferred embodiment in FIG. 1 where the matrix patch of the present invention extends to a desired amount beyond the width of the digit being treated. This additional length allows the matrix patch to be adhered to the sides and perhaps the bottom (opposite the nail) of the treated digit. This provides additional contact between the matrix patch of the present invention and the epidermis tissue surrounding the nail in need of treatment. In this manner the drug is administered to the infected digit from numerous directions simultaneously. The matrix patch of the present invention can thus deliver the pharmaceuticle agent into the nail, through the cuticle and through contacted epidermis simultaneously.

DETAILED DESCRIPTION OF THE PREFERRED EMBODIMENTS

The following definitions, when used, will be helpful in describing the invention and will eliminate the need for repetitive explanations.

When used in context, the terms "enhancement," "penetration enhancement" or "permeation enhancement" relate to an increase in the permeability of a biological membrane (i.e. skin and/or nail) to a drug, so as to increase the rate at which the drug permeates through the membrane. The enhanced permeation effected though the use of such enhancers can be observed, for example, by measuring the rate of diffusion of the drug through animal or human skin using a diffusion cell apparatus. The diffusion cell is described by Merritt et al. Diffusion Apparatus for Skin Penetration, *J. of Controlled Release*, 1 (1984) pp. 161–162.

By "afflicted situs" is meant a localized area of pathology, discomfort, infection, inflammation or lesion, and the immediately surrounding area, e.g. the nail and surrounding area of a finger or toe.

By the term "permeant" or "drug" is meant any chemical material or compound suitable for transdermal or transnail administration which includes a desired biological or pharmacological effect by topical application to the "affliction situs." In general, this includes therapeutic agents such as antibiotics and antifungal agents. The term "permeant" is also meant to include mixtures. By mixtures is meant combinations of permeants from different categories, mixtures of permeants from the same category and mixtures of free base and salt forms of the same or different permeants from the same or different categories.

By "effective" amount of a drug or permeant is meant a nontoxic but sufficient amount of a compound to provide the desired local effect. An "effective" amount of permeation enhancer as used herein means an amount selected so as to provide the desired increase in membrane permeability and, correspondingly, the desired depth of penetration, rate of administration and amount of drug.

By "drug delivery system," "drug/enhancer composition" or any similar terminology is meant a formulated composition containing the drug to be transdermally or transnailly delivered in combination with such pressure sensitive adhesives, penetration enhancers, excipients, or any other additives.

By the term "matrix" or "matrix system" is meant an active permeant homogeneously combined in a biocompatible pressure sensitive adhesive which may or may not also contain other ingredients or in which the enhancer is also homogeneously dissolved or suspended. A matrix system is usually an adhesive patch having an impermeable film backing and, before transdermal/transnail application, a release liner on the surface of the adhesive opposite the film backing. A matrix system therefore is a unit dosage form of a drug composition in an adhesive carrier, also containing the enhancer and other components which are formulated for maintaining the drug composition in the adhesive in a drug transferring relationship with the skin and nail.

As noted above, the drug delivery device is a matrix formulation where the permeant and enhancer are incorporated into an adhesive layer. In formulations where the enhancer is incorporated into the adhesive, the enhancer will generally be present in amounts of between about 0.1 to 30% by weight, preferably between about 1 to 20% by weight and most preferably between about 2 to 20% by weight. The matrix device is brought in contact with the skin and nail at the afflicted situs and is held in place by a suitable adhesive.

It is to be understood that while the invention has been described in conjunction with the preferred specific embodiments thereof, that which follow are intended to illustrate and not limit the scope of the invention. Other aspects of the invention will be apparent to those skilled in the art to which the invention pertains.

In the matrix systems the carrier is primarily the pressure sensitive adhesive in which the enhancer and an effective amount of an active permeant or drug are homogeneously combined.

Suitable pressure sensitive adhesives may include acrylic copolymer adhesives or "acrylic adhesive," (e.g. National Starch Durotak 80-1196 and Monsanto Gelva 737), rubber based adhesives or "rubber adhesive," such as polyisobutylene or "PIB adhesive," (e.g. Adhesive Research MA-24) and silicone based adhesives or "silicone adhesive," (e.g. Dow Bio-PSA). However, any other suitable pressure sensitive adhesives may also be used which are compatible with the active permeant and enhancer when utilized.

Suitable enhancers are well known in the art and may include representative members selected from the group consisting of a-hydroxy acids and fatty acid esters and amides thereof, fatty alcohols, fatty acids, $C_1$ to $C_8$ esters of fatty acids, $C_1$ to $C_{18}$ esters of glycerol and the like.

In matrix systems, the adhesive is present in amounts ranging from 50 to 99.75% by weight and will preferably be present in amounts of between about 70 and 99.5% by weight. The enhancer is also homogeneously dissolved or suspended in the adhesive matrix and when present is present in amounts of between about 0.1–30% by weight with ranges of between about 1 to 20% w being preferred and 2.0 to 15% w being most preferred.

EXAMPLES AND PREFERRED EMBODIMENTS

I. Skin Flux Methodology

In vitro human cadaver skin flux studies were conducted using modified Franz non-jacketed permeation cells. The temperature of the skin surface was maintained at 32° C. by placing the cells in a circulating water bath positioned over a stirring module. The epidermal membrane was separated from the dermatomed human cadaver skin by the heat-separation method of Kligman and Christopher (*Arch. Dermatol.* 88:702 (1963)) involving the exposure of the full thickness skin to 60° C. heat for 60 seconds, after which time the stratum corneum and the epidermis (epidermal membrane) were gently peeled off the dermis.

For a matrix skin flux study, the heat separated human epidermal membrane was cut into rectangular strips. The matrix was cut into 0.71 cm² circular discs. The release liner was peeled and discarded and the matrix disc was laminated onto the stratum corneum surface of the epidermal membrane. The skin-matrix sandwich was then loaded onto the diffusion cells. Each piece of the skin matrix sandwich was loaded between the donor and receiver compartments of a diffusion cell, with the epidermal side facing the receiver compartment, and clamped in place. The receiver compartment was then filled with 0.02% sodium azide aqueous solution. The solubility of the drug in this medium is adequate to ensure sink conditions throughout the experiment. The diffusion cell was then placed in a circulating water bath calibrated to maintain the skin surface temperature at 32±1° C. At predetermined sampling intervals, the entire contents of the receiver compartment were collected for drug quantitation and the receiver compartment was filled with fresh receiver solution, taking care to eliminate any air bubbles at the skin/solution interface.

For the topical gel study, included for illustration purposes, a thin film of gel approximately 10 μl/cm², was applied to the stratum-corneum surface of a hydrated piece of human cadaver skin. The skin was placed on top of the diffusion cell with the epidermal side toward the receiver compartment and clamped in place with an open-top lid. The gel was unoccluded and exposed to the ambient conditions of the laboratory. At predetermined sampling intervals, the entire contents of the receiver compartment were collected for drug quantitation.

The cumulative amount of drug permeated per unit area at any time $t(Q_t, \mu g/cm^2)$ was determined as follows:

$$Q_t = \sum_{n=0}^{t} (C_n * V) / A$$

where $C_n$ is the concentration (μg/ml) of the drug in the receiver sample for the corresponding sample time, V is the volume of fluid in the receiver chamber (~6.3 cm³), and A is the diffusion area of the cell (0.64 cm²).

To determine the amount of drug retained in the skin, the patch was removed from the skin after duration of study. Circular skin of area 0.71 cm² that was in contact with the matrix patch was punched out. All punched skin pieces were dried overnight in an oven at 36° C., weighed and transferred to scintillation vial containing 5 ml methanol as extraction solvent. The scintillation vials were shaken in a gyrorotatory lab shaker for 12 hours and the amount of drug extracted in the solution was analyzed.

II. Nail Flux Methodology

In vitro human cadaver nail flux studies were conducted using modified Franz non-jacketed permeation cells. The temperature of the nail surface was maintained at 32° C. by placing the cells in a circulating water bath positioned over a stirring module. Human finger nail or toe nail was stored under frozen conditions in 0.02% (w/v) sodium azide solution. Nails that were greater than 1 cm² in area were used for the flux studies. Nails with dorsal side facing the donor compartment were sandwiched between two layers of a closed cell polyethylene foam film. Annular ring of 2.38 cm outer diameter and 0.95 cm inner diameter was cut from the backing film. The area of the donut hole (0.97 cm²) is large enough to provide complete contact with the receiver media. The purpose of the foam backing film was to prevent any leakage of receiver medium from the cell assembly. The nails were allowed to hydrate at 32° C. overnight with 0.02% (w/v) sodium azide solution in the receiver compartment. The following morning, 0.71 cm² circular matrix patches were laminated onto the dorsal side of the nail. Each nail matrix sandwich was then loaded between the donor and receiver compartments of a diffusion cell, with the ventral side of nail facing the receiver compartment, and clamped in place.

To determine the amount of drug retained in the nails, the patch was removed from the nail after duration of study. Circular nail of area 0.71 cm² that was in contact with the matrix patch was punched out and examined. All punched nails were dried overnight in an oven at 36° C., weighed and transferred to scintillation vial containing 5 ml dimethyl sulfoxide as extracting solvent. The scintillation vials were shaken in a gyrotory lab shaker for 12 hours and the amount of drug extracted in the solution was analyzed. The remaining portion of nail was also dried, weighed, extracted in dimethyl sulfoxide and analyzed for drug content. Completeness of extraction was verified by drying the extracted nails, and re-extracting them in 3 ml dimethyl sulfoxide for 12 hours. No drug was seen when the re-extracted samples were analyzed.

III. Nail Flux Studies

Example 1

Fluconazole is an antifungal drug, commonly used for systemic fungal infections. Clinical studies have already proved that fluconazole could be administered orally for treatment of Onychomycosis. Matrix patches containing varying amounts of antifungal agent and enhancers were prepared and tested. The matrix systems consisted of 2 to 10% by weight of fluconazole, and 0 to 20% by weight of lauroyl lactylic acid as an enhancer in a medical grade acrylic copolymer adhesive (Durotak 87-2516).

The matrix formulations were prepared as follows. First, the solids content of the adhesive was determined by weighing a small amount of the adhesive solution in a pre-weighed aluminum dish. The solvent was evaporated by overnight drying in a convection oven maintained at 70° C. and the weight of the residue (dry adhesive) and percent solid adhesive content of the solution was determined. Once the solids content was determined, a known weight of the acrylic copolymer adhesive solution was weighed into a glass bottle. From the weight of the adhesive solution and the percent solid adhesive content, the amount of adhesive in the solution was calculated. The antifungal drug and the enhancers were added to the bottle in the required proportions to yield the desired final composition. The bottle was then tightly capped, sealed with parafilm and rotated overnight until all ingredients had completely dissolved and the resultant solution was visually clear.

Approximately 8 ml of the solution was then dispensed on a silanized polyester release liner and cast with a 10 mil gap casting knife. The casting was then dried in a convection oven at 70° C. for 15 minutes to evaporate the solvent and to yield a dried film approximately 2.0 mil thick. A 3 mil thick polyethylene backing film was laminated onto the dried adhesive film with a rubber roller. These matrix laminates were then used to conduct in vitro nail flux studies as described. The results of the nail flux experiments are presented in Tables 1 and 2.

TABLE 1

| Formulation A/D/E* | Composition (% w/w) | $Q_t$ (t = 24) ($\mu g/cm^2$)** | $Q_t$ (t = 48) ($\mu g/cm^2$)** | $Q_t$ (t = 72) ($\mu g/cm^2$)** | $Q_t$ (t = 96) ($\mu g/cm^2$)** | $Q_t$ (t = 144) ($\mu g/cm^2$)** |
|---|---|---|---|---|---|---|
| A/D | 94/6 | 0 | 0 | 0 | 0 | 9.04 ± 10.24 |
| A/D/E | 84/6/10 | 0 | 0 | 0 | 0 | 3.07 ± 3.88 |

*A = Adhesive, (Durotak 87-2516, an acrylic polymer); D = Drug, (Fluconazole); E = Enhancer, (lauroyl Lactylic acid)
**(Mean ± SD), n = 4 donors, 4 cell.

TABLE 2

| Formulation A/D/E* | Composition (% w/w) | $Q_t$ (t = 48) (flux) ($\mu g/cm^2$)** | $Q_t$ (t = 48) (in the nail) ($\mu g/g$)** |
|---|---|---|---|
| A/D/E | 88/2/10 | 0 | 490.61 ± 146.71 |
| A/D/E | 86/4/10 | 0 | 1266.61 ± 408.78 |
| A/D/E | 84/6/10 | 0 | 1702.19 ± 882.61 |
| A/D/E | 82/8/10 | 0 | 2549.83 ± 969.55 |

*A = Adhesive, (Durotak 87-2516; an acrylic polymer) D = Drug, (Fluconazole); E = Enhancer, (lauroyl lactylic acid).
**(Mean ± SD), n = 4 donors, 6 cell.

Table 1 shows that there is no permeation of fluconazole across the nail up to 96 hours and very low amounts permeate after a week. This illustrates that the nail is a formidable barrier to penetration and only minute quantities of fluconazole can reach the nail bed by permeation through the nail. Also, it can be seen from Table 2 that significant amount of drug penetrates into and is retained in the nail, illustrating the nail's capacity for binding and retaining the drug. The amount of fluconazole retained in the nail increases with increase in the drug concentration in the formulation. However, it is noted that some permeation of the antifungal agent through the nail was observed after 144 hours of patch application according to the present invention.

Example II

The equilibration time of fluconazole into the nail was evaluated. At each time point, the amount of drug (Q) in the nail per unit dry weight of nail and the amount of drug in receiver media was determined. There was no flux of fluconazole across the nails. The amount of drug retained in the nails is shown in the tables below.

TABLE 3

| Formulation A/D/E* | Composition (% w/w) | $Q_t$ (t = 24) (μg/g)** | $Q_t$ (t = 48) (μg/g)** | $Q_t$ (t = 72) (μg/g)** | $Q_t$ (t = 96) |
|---|---|---|---|---|---|
| A/D | 94/6 | 1985.96 ± 891.06 | 2513.49 ± 699.77 | 2178.54 ± 756.61 | 1570.46 ± 464.17 |
| A/D/E | 84/6/10 | 1894.06 ± 609.25 | 2137.26 ± 419.90 | 2095.13 ± 896.56 | 1571.91 ± 569.31 |

*A = Adhesive, (Durotak 87-2516, an acrylic polymer); D = Drug, (Fluconazole); E = Enhancer, (lauroyl lactylic acid).
**(Mean ± SD), n = 4 donors, 4 cell.

TABLE 4

| Formulation A/D/E* | Composition (% w/w) | $Q_t$ (t = 48) (μg/g)** |
|---|---|---|
| A/D | 94/6 | 1517.52 ± 569.92 |
| A/D/E | 89/6/5 | 2183.45 ± 303.36 |

*A = Adhesive, (Durotak 87-2516, acrylic polymer); D = Drug, (Fluconazole); E = Enhancer, (sorbitan monooleate).
**(Mean ± SD), n = 4 donors, 7 cell.

It is seen from Tables 3 and 4 that the amount of fluconazole partitioning into the nail reaches an equilibrium value within 24 hours. The literature reports that when 50 mg/day of fluconazole was orally administrated for up to 14 days, the amount of fluconazole in the nail was: 1.31 μg/g at day 1 and 1.81 μg/g at day 14["Pharmacokinetic evaluation of fluconazole in skin and nails," Hay R. J., *International Journal of Dermatology*, 1992 31 (supplement 2) page 6–7]. Clearly, the data in this example shows approximately 1000–2000 times higher amounts of fluconazole in the nail after 48 hours of patch application compared to the reported amount of fluconazole in the nail after oral administration.

Example III

Terbinafine hydrochloride is another antifungal drug which is approved for the treatment of Onychomycosis and other fungal infections. Matrix systems were prepared as in Example 1. Flux of terbinafine hydrochloride across the nail and the amount of drug in the nail from matrix patch was also evaluated. The results are given in Tables 5–6.

TABLE 5

| Formulation A/D/E* | Composition (% w/w) | $Q_t$ (t = 24) (μg/cm²)** | $Q_t$ (t = 48) (μg/cm²)** | $Q_t$ (t = 72) (μg/cm²)** | $Q_t$ (t = 96) (μg/cm²)** |
|---|---|---|---|---|---|
| A/D | 97.5/2.5 | 0 | 0 | 0 | 0 |
| A/D/E | 92.5/2.5/5 | 0 | 0 | 0 | 0 |

*A = Adhesive, (Durotak 87-2516, an acrylic polymer); D = Drug, (Terbinafine-HCl); E = Enhancer, (triacetin).
**(Mean ± SD), n = 2 donors, 2 cell.

TABLE 6

| Formulation A/D/E* | Composition (% w/w) | $Q_t$ (t = 24) (μg/cm²)** | $Q_t$ (t = 48) (μg/cm²)** | $Q_t$ (t = 72) (μg/cm²)** | $Q_t$ (t = 96) (μg/cm²)** |
|---|---|---|---|---|---|
| A/D | 97.5/2.5 | 57.19 ± 22.33 | 212.65 ± 267.17 | 72.68 ± 17.26 | 353.42 ± 29.24 |

TABLE 6-continued

| Formulation A/D/E* | Composition (% w/w) | $Q_t$ (t = 24) (μg/cm²)** | $Q_t$ (t = 48) (μg/cm²)** | $Q_t$ (t = 72) (μg/cm²)** | $Q_t$ (t = 96) (μg/cm²)** |
|---|---|---|---|---|---|
| A/D/E | 92.5/2.5/5 | 76.53 ± 28.04 | 155.16 ± 156.36 | 212.81 ± 233.03 | 93.92 ± 11.92 |

*A = Adhesive, (Durotak 87-2516, an acrylic polymer); D = Drug, (Terbinafine-HCl); E = Enhancer, (triacetin).
**(Mean ± SD), n = 2 donors, 2 cell.

The results in Table 5 show that there is no permeation of terbinafine across the nail up to 96 hours. However, significant amount of drug penetrates into and is retained in the nail as shown in Table 6. The amount of drug retained in the nail per unit dry weight of nail was determined. The literature reports that when 250 mg/day of terbinafine was orally administrated for up to 14 days, the amount of terbinafine in the nail was: 0.22 μg/g at day 7 and 0.52 μg/g at day 14["Levels of terbinafine in plasma, stratum corneum, dermis-epidermis (without stratum corneum), sebum, hair, and nails during and after 250 mg terbinafine orally once daily for 7 and 14 days," Faergemann J, Zehender H, Millerious L., *Clinical and Experimental Dermatology*, 1994: 19, pgs 121–126]. Clearly, the results from Table 6 show *Experimental Dermatology*, 1994: 19, pgs 121–126]. Clearly, the results from Table 6 show approximately 100–1000 times higher amount of terbinafine in the nail after 48 hours of patch application compared to the amount of terbinafine in the nail after the reported oral administration.

Example IV

Again following the procedure of Example 1. The flux of another common antifungal drug, clotrimazole, across the nail and the amount of drug in the nail from matrix patch was also evaluated. The results are given in Tables 7–8.

TABLE 7

| Formulation A/D/E* | Composition (% w/w) | $Q_t$ (t = 24) (μg/cm²)** | $Q_t$ (t = 48) (μg/cm²)** | $Q_t$ (t = 72) (μg/cm²)** | $Q_t$ (t = 96) (μg/cm²)** |
|---|---|---|---|---|---|
| A/D | 94/6 | 0 | 0 | 0 | 0 |
| A/D/E | 84/6/10 | 0 | 0 | 0 | 0 |

*A = Adhesive, (Durotak 87-2516, an acrylic polymer); D = Drug, (Clotrimazole); E = Enhancer, (lauramide diethanolamine).
**(Mean ± SD), n = 3 donors, 3 cell.

TABLE 8

| Formulation A/D/E* | Composition (% w/w) | $Q_t$ (t = 24) (μg/g)** | $Q_t$ (t = 48) (μg/g)** | $Q_t$ (t = 72) (μg/g)** | $Q_t$ (t = 96) (μg/g)** |
|---|---|---|---|---|---|
| A/D | 94/6 | 530.68 ± 536.30 | 777.36 ± 196.19 | 1052.34 ± 885.93 | 521.62 ± 244.22 |
| A/D/E | 84/6/10 | 213.38 ± 73.12 | 556.79 ± 320.24 | 601.80 ± 503.26 | 560.73 ± 273.84 |

*A = Adhesive, (Durotak 87-2516, an acrylic polymer); D = Drug, (Clotrimazole); E = Enhancer, (lauramide diethanolamine).
**(Mean ± SD), n = 3 donors, 3 cell.

The results in Table 7 show that there is no permeation of clotrimazole across the nail up to 96 hours. However, Table 8 shows significant amount of drug penetrates into and is retained in the nail. The amount of drug retained in the nail per unit dry weight of nail after 48 hours of application of patch was greater than 500 μg/g.

IV Skin Flux Studies

Example V

Following the procedure outlined above, the flux of fluconazole across the human cadaver skin was evaluated in different studies. The effect of increasing drug concentration on skin flux of fluconazole and the amount of drug retained in the skin were also determined. The results are presented in Tables 9–11 below.

TABLE 9

| Formulation A/D/E* | Composition (% w/w) | $Q_t$ (t = 24) ($\mu$g/cm$^2$)** |
|---|---|---|
| A/D | 94/6 | 47.43 ± 39.14 |
| A/D/E | 89/6/5 | 52.44 ± 55.51 |

*A = Adhesive, (Durotak 87-2516, an acrylic polymer); D = Drug, (Fluconazole); E = Enhancer, (sorbitan monooleate).
**(Mean ± SD), n = 10 skins, 40 cells.

TABLE 10

| Formulation A/D/E* | Composition (% w/w) | $Q_t$ (t = 24) ($\mu$g/cm$^2$)** |
|---|---|---|
| A/D/E | 88/2/10 | 20.44 ± 12.39 |
| A/D/E | 86/4/10 | 41.17 ± 16.30 |
| A/D/E | 84/6/10 | 61.42 ± 31.21 |
| A/D/E | 82/8/10 | 53.68 ± 49.93 |

*A = Adhesive, (Durotak 87-2516, an acrylic polymer); D = Drug, (Fluconazole); E = Enhancer, (lauroyl lactylic acid).
**(Mean ± SD), n = 3 skins, 12 cells.

TABLE 11

| Formulation A/D/E* | Composition (% w/w) | $Q_t$ (t = 24) (in the skin) ($\mu$g/cm$^2$)** |
|---|---|---|
| A/D | 94/6 | 6845.15 ± 1950.52 |
| A/D/E | 89/6/5 | 7473.76 ± 1590.36 |

*A = Adhesive, (Durotak 87-2516, an acrylic polymer); D = Drug, (Fluconazole); E=Enhancer, (sorbitan monooleate).
**(Mean ± SD), n = 3 skins, 12 cells.

When compared with Example 1, the skin flux of fluconazole shown in table 9 is much higher than the nail flux. It can be seen from Table 10 that the optimal skin flux is observed with a formulation containing 6% (w/w) fluconazole. Amount of fluconazole retained in the skin after a flux of 24 hours is shown in Table 11. The literature reported that when 50 mg/day of fluconazole was orally administrated for up to 14 days, the amount of fluconazole in the skin was: 11.70 $\mu$g/g at day 1 and 24.15 $\mu$g/g at day 14 ["Pharmacokinetic evaluation of fluconazole in skin and nails," Hay R. J., *International Journal of Dermatology*, 1992: 31 (supplement 2), pgs 6–7]. Clearly, the data in this example show approximately 500–600 times higher amount of fluconazole in the skin at 24 hours compared to the amount of fluconazole in the skin at day 1 after oral administration as reported in the literature. The effect of different enhancers on the skin flux of fluconaaole, and the flux with different adhesives were also evaluated. These results are summarized in Tables 12–14.

TABLE 12

| Formulation A/D/E* | Composition (% w/w) | $Q_t$ (t = 24) ($\mu$g/cm$^2$)** |
|---|---|---|
| A/D | 94/6 | 54.88 ± 39.04 |
| A/D/E | 84/6/10 | 123.64 ± 61.99 |

*A = Adhesive, (Durotak 87-2516); D = Drug, (Fluconazole); E = Enhancer, lauric diethanolamide.
**(Mean ± SD), n = 3 skins, 12 cells.

TABLE 13

| Formulation A/D/E* | Composition (% w/w) | $Q_t$ (t = 24) ($\mu$g/cm$^2$)** |
|---|---|---|
| A/D | 98/2 | 2.92 ± 2.67 |
| A/D/E | 88/2/10 | 4.39 ± 2.21 |

*A = Adhesive, (TSR, an acrylic polymer) D = Drug, (Fluconazole); E = Enhancer, (lauroyl lactylic acid).
**(Mean ± SD), n = 3 skins, 12 cells.

TABLE 14

| Formulation A/D/E* | Composition (% w/w) | $Q_t$ (t = 24) ($\mu$g/cm$^2$)** |
|---|---|---|
| A/D | 90/10 | 27.42 ± 22.81 |
| A/D/E | 80/10/10 | 74.00 ± 21.93 |

*A = Adhesive, (Gelva-737, an acrylic polymer); D = Drug, (Fluconazole); E = Enhancer, (lauroyl lactylic acid).
**(Mean ± SD), n = 2 skins, 8 cells.

The results shown in Table 12–14 illustrate the high skin flux of fluconazole using various pressure sensitive adhesives with and without the presence of an enhancer. Even without an enhancer, there is sufficient flux shown to be somewhat effective. However, the presence of an enhancer, such as lauroyl lactylic acid or lauric diethanolamide significantly increases the flux in each adhesive type. The high skin flux and skin retention is likely to lead to lateral diffusion of drug into the nail bed.

Example VI

The effect of occlusion on the skin flux of fluconazole was evaluated. Matrix systems of identical compositions with occlusive or non-occlusive backing films were loaded on skin. The procedures of Example 1 were followed with the exception that the casting was with a 5 mil gap casting knife. The results are shown in Table 15 below.

TABLE 15

| Formulation A/D/E* | Composition (%wlw) | Backing Film | $Q_t$ (t = 24) ($\mu$g/cm$^2$)** |
|---|---|---|---|
| A/D | 94/6 | Occlusive | 7.55 ± 5.97 |
| A/D/E | 84/6/10 | Occlusive | 32.66 ± 27.74 |
| A/D | 94/6 | Non-occlusive | 3.74 ± 1.16 |
| A/D/E | 84/6/10 | Non-occlusive | 6.87 ± 4.44 |

*A = Adhesive, (Durotak 2516, an acrylic polymer); D = Drug, (Fluconazole); E = Enhancer, (lauroyl lactylic acid).
**(Mean ± SD), n = 3 skins, 12 cells.

Without taking into consideration the mean deviations, in formulations not containing an enhancer, the skin flux from the formulation having the occlusive backing film shows about twice the rate as with the formulation containing the non-occlusive backing. In formulations containing an enhancer, the flux rate of the occlusive formulation increases to about five times the rate on the non-occlusive counterpart.

Example VII

Topical preparation of fluconazole were made on a 10 ml scale. Ten milliliters of a solution made up of 65 parts by weight ethanol, 20 parts by weight water and 15 parts by weight glycerin was used as a base. To this was added 600 mg of fluconazole in a vial which was capped and ultrasonicated to completely dissolve the drug. Then 300 mg of hydroxypropylmethyl cellulose (Methocel E10M) was added as a gelling agent and the contents were mixed thoroughly and gently rotated overnight to completely dissolve the gelling agents. This resulted in a gel having a gel/drug (G/D) weight composition of about 94/6. The procedure mentioned above for the testing of topical gels was followed, and the skin flux from the topical gel, without occlusion, and a matrix patch having about the same drug concentration, were compared. The results are given in Table 16.

TABLE 16

| Formulation A/D* | Composition (% w/w) | $Q_t$ (t = 24) ($\mu g/cm^2$)** |
|---|---|---|
| A/D | 94/6 | 11.41 ± 5.36 |
| G/D | 94/6 | 4.61 ± 2.34 |

*A = Adhesive, (Durotak 87-2516, an acrylic polymer); D = Drug, (Fluconazole).
**(Mean ± SD), n = 3 skins, 12 cells.

As shown in Table 16, the flux from the matrix systems is about 3 times higher than the flux from topical formulation.

Example VIII

Following the procedure from the above examples, the flux of terbinafine hydrochloride across the human cadaver skin was evaluated in different studies. The effect of increasing drug concentration, and increasing enhancer concentration on skin flux of terbinafine hydrochloride were evaluated. The amount of drug retained on skin after application of the patch for 1 day was also determined. The results are presented in Tables 17–19 below.

TABLE 17

| Formulation A/D/E* | Composition (% w/w) | $Q_t$ (t = 24) ($\mu g/cm^2$)** |
|---|---|---|
| A/D | 96/4 | 1.55 ± 0.40 |
| A/D/E | 87.5/4/8.5 | 2.73 ± 0.56 |

*A = Adhesive, (Durotak 87-2516, an acrylic polymer); D = Drug, (Terbinafine-HCl); E = Enhancer, (Triacetin).
**(Mean ± SD), n = 3 skins, 12 cells.

The results shown in Table 17 illustrate the flux of terbinafine-HCl using an acrylic pressure sensitive adhesive with and without the presence of an enhancer. Even without an enhancer, there is sufficient flux. However, the presence of an enhancer, triacetin, significantly increases the flux.

TABLE 18

| Formulation A/D/E* | Composition (% w/w) | $Q_t$ (t = 24) ($\mu g/cm^2$)** |
|---|---|---|
| A/D/E | 91/1/8 | 0.77 ± 0.32 |
| A/D/E | 90/2/8 | 1.55 ± 0.52 |
| A/D/E | 89.5/2.5/8 | 2.32 ± 1.30 |
| A/D/E | 89/3/8 | 2.30 ± 1.26 |

*A = Adhesive, (Durotak 87-2516, an acrylic polymer); D = Drug, (Terbinafine-HCl); E = Enhancer, (Triacetin).
**(Mean ± SD), n = 3 skins, 12 cells.

The results shown in Table 18 illustrate the flux of terbinafine-HCl using an acrylic pressure sensitive adhesive with and without the presence of an enhancer. Even without an enhancer, there is sufficient flux shown to be somewhat effective. However, the presence of an enhancer, triacetin, significantly increases the flux.

TABLE 19

| Formulation A/D/E* | Composition (% w/w) | $Q_t$ (t = 24) ($\mu g/cm^2$)** |
|---|---|---|
| A/D | 97.5/2.5 | 0.77 ± 0.27 |
| A/D/E | 92.5/2.5/5 | 1.15 ± 0.40 |
| A/D/E | 87.5/2.5/10 | 1.73 ± 0.83 |
| A/D/E | 82.5/2.5/15 | 1.97 ± 0.41 |
| A/D/E | 77.5/2.5/20 | 3.05 ± 1.07 |

*A = Adhesive, (Durotak 87-2516, an acrylic polymer); D = Drug, (Terbinafine-HCl); E = Enhancer, (triacetin).
**(Mean ± SD), n = 3 skins, 12 cells.

The results in Table 19 show that by increasing the triacetin concentration there is a consistant increase in the skin flux.

Example IX

The flux of other representative antifungal agents, i.e. clotrimazole, ketoconazole, and miconazole, in matrix formulations, with and without enhancers, are evaluated in Tables 20–23.

TABLE 20

| Formulation A/D/E* | Composition (% w/w) | $Q_t$ (t = 24) ($\mu g/cm^2$)** |
|---|---|---|
| A/D | 95/5 | 0.00 ± 0.00*** |
| A/D/E | 85/5/10 | 18.40 ± 6.99 |

*A = Adhesive, (TSR, an acrylic copolymer); D = Drug, (Clotrimazole); E = Enhancer, (glycolic acid).
**(Mean ± SD), n = 3 skins, 12 cells.
***Less than detection limit, which is $Q_t \leq 3 \mu g/cm^2/t$.

These results indicate clotrimazole flux, without an enhancer, was below the detection limit. However, in the presence of glycolic acid as an enhancer there was significant flux from a matrix.

TABLE 21

| Formulation A/D/E* | Composition (% w/w) | $Q_t$ (t = 24) ($\mu g/cm^2$)** |
|---|---|---|
| A/D | 94/6 | 0.84 ± 0.28 |
| A/D/E | 84/6/10 | 2.45 ± 0.41 |

*A = Adhesive, (Durotak 87-2516, an acrylic polymer); D = Drug, (Clotrimazole); E = Enhancer, (lauramide-diethanolamine).
**(Mean ± SD), n = 5 skins, 20 cells.

The results shown in Table 21 illustrate the flux of clotrimazole using an acrylic pressure sensitive adhesive with and without the presence of an enhancer. While there is measurable flux without an enhancer, the presence of an enhancer, lauramide-DEA, significantly increases the flux.

TABLE 22

| Formulation A/D/E* | Composition (% w/w) | $Q_t$ (t = 24) ($\mu g/cm^2$)** |
|---|---|---|
| A/D | 97/3 | 1.81 ± 0.62 |
| A/D/E | 87/3/10 | 3.41 ± 1.83 |

*A = Adhesive, (Durotak 87-2516, an acrylic polymer); D = Drug, (Ketoconazole); E = Enhancer, (lauramide-diethanolamine).
**(Mean ± SD), n = 3 skins, 12 cells.

The results shown in Table 22 illustrate the flux of ketoconazole using an acrylic pressure sensitive adhesive with and without the presence of an enhancer. While there is some flux without an enhancer, the presence of an enhancer, lauramide-DEA, doubles the flux.

TABLE 23

| Formulation A/D/E* | Composition (% w/w) | $Q_t$ (t = 24) ($\mu g/cm^2$)** |
|---|---|---|
| A/D | 90/10 | 2.36 ± 1.12 |
| A/D/E | 70/10/20 | 4.38 ± 1.35 |

*A = Adhesive, (TSR, an acrylic polymer); D = Drug, (Miconazole); E = Enhancer, (triacetin).
**(Mean ± SD), n = 5 skins, 20 cells.

The results shown in Table 23 illustrate the flux of miconazole using TSR as a pressure sensitive adhesive with and without the presence of an enhancer. While there is some flux without an enhancer, the presence of triacetin as an enhancer, significantly increases the flux. These examples demonstrate how the matrix patch of the present invention is able to simultaneously facilitate significant drug flux across the epidermis and increase the concentrations of the desired drug into the nail. This simultaneous delivery provides a dual pathway attack for combatting the infection. The administration of the antifungal agent into the nail precludes additional migration or growth of the fungus further into the nails and the administration of antifungal agents into the skin around the nail facilitates a more direct application to the infected area. In this manner, the matrix patch delivers the antifungal agent into both the infected nail and the skin around the nail, enhancing drug delivery to the infected area as compared to previously known techniques, methods and compositions.

While certain antifungal agents, pressure sensitive adhesives and enhancers have been primarily used for purposes of illustration, other active agents, adhesives and enhancers may also be utilized which result in transdermal/transnail flux and drug retention.

Example X

Matrix patch devices, as shown in FIG. 2, are prepared having various surface areas sufficient to cover toe nails and surrounding skin area of each toe on a foot. Each device consists of an impermeable occlusive backing layer and a matrix layer of an acrylic adhesive (Durotak 87-2516), fluconazole and a lauroyl lactylic acid enhancer having the compositions shown in Table 2. Patches are applied to the nails and surrounding skin of toes of volunteers who wear patches for a period of up to four days without restricting normal activity. Patches are shown to adhere to the toes for the duration of the tests without causing skin irritation, without affecting normal activity and without any noticable discomfort. No attempt is made to determine skin flux or nail retention of the drug.

Within the guidelines presented herein, a certain amount of experimentation to obtain optimal formulations can be carried out by those skilled in the art. What is important is that the matrix system must be configured to cover the nail and surrounding skin area of the digit being treated. The degree or distance of surrounding skin coverage is limited only by the functionality of the digit. In other words, there should be sufficient skin area coverage to provide for flux of the drug through the skin layer to the nail bed but not so much as to inhibit the flexability of the digit. That can be readily determined by the size of the digit to be treated. One or more digits of the same foot or hand may be treated simultaneously. Therefore, the invention is limited in scope only by the following claims and functional equivalents thereof.

What is claimed is:

1. A device for the treatment of infections of the nail comprising:
    (a) an occlusive backing layer and;
    (b) a matrix layer having a first surface and a second surface opposite the first surface where the first surface is adhered to the backing layer and the second surface being adapted to be in diffusional contact with the nail and surrounding skin, said matrix layer comprising:
        i) a pressure sensitive adhesive; and
        ii) an amount of an antifungal agent which is sufficient to provide an antifungal effect contained in said adhesive, wherein said antifungal agent is a member selected from the group consisting of: fluconazole, terbinafine, clotrimazole, miconazole and ketoconazole, salts thereof, and a mixture thereof;
    said device being configured such that, when applied to a nail, the second surface of the matrix layer will be adhesively secured to and cover the nail and surrounding skin area.

2. A device according to claim 1 wherein the antifungal agent is present in amounts of between about 1% and 10% by weight of the matrix layer.

3. A device according to claim 2 wherein the matrix layer additionally uniformly contains an amount of a permeation enhancer which is sufficient to increase permeation of the antifungal agent into the nail and surrounding skin area.

4. A device according to claim 3 wherein the enhancer is present in amounts of between about 0.1% to 30% by weight of the matrix layer.

5. A device according to claim 4 wherein the pressure sensitive adhesive is a member selected from the group consisting of acrylic, urethane rubber, silicone adhesives, and a mixture thereof.

6. A method for the transdermal/transnail treatment of an infected nail on a hand or foot with an antifungal agent comprising adhesively securing to the nail and surrounding skin of said nail an adhesive device comprising:
    (a) an occlusive backing layer; and
    (b) a matrix layer, one surface of which is adhered to the backing layer and the other surface being secured in diffusional contact with the infected nail and the surrounding skin, said matrix layer comprising:
        i) a pressure sensitive adhesive; and
        ii) an amount of an antifungal agent which is sufficient to provide an antifungal effect contained in said adhesive, wherein said antifungal agent is a member selected from the group consisting of: fluconazole, terbinafine, clotrimazole, miconazole, ketoconazole, salts thereof, and a mixture thereof;

said device being adhesively secured to said nail and adjacent surrounding skin area for a time sufficient to deliver an effective amount of said antifungal agent to the area of infection.

7. A method according to claim 6 wherein the antifungal agent is present in amounts of between about 1% and 10% by weight of the matrix layer.

8. A method according to claim 7 wherein the matrix layer additionally uniformly contains an amount of a permeation enhancer which is sufficient to increase permeation of the antifungal agent into the nail and surrounding skin area.

9. A method according to claim 8 wherein the enhancer is present in amounts of between about 0.1% to 30% by weight of the matrix layer.

10. A device according to claim 9 wherein the pressure sensitive adhesive is a member selected from the group consisting of acrylic, urethane rubber, silicone adhesives, and a mixture thereof.

* * * * *